United States Patent [19]

Ryan et al.

[11] Patent Number: 4,900,540
[45] Date of Patent: * Feb. 13, 1990

[54] LIPISOMES CONTAINING GAS FOR ULTRASOUND DETECTION

[75] Inventors: Patrick J. Ryan, Worcester; Michael A. Davis, Westwood; Donald L. Melchior, Framingham, all of Mass.

[73] Assignee: Trustees of the University of Massachusetts, Amherst, Mass.

[*] Notice: The portion of the term of this patent subsequent to Jan. 1, 2002 has been disclaimed.

[21] Appl. No.: 505,697

[22] Filed: Jun. 20, 1983

[51] Int. Cl.$^4$ .................. A61K 49/00; G01N 31/00
[52] U.S. Cl. ............................... 424/9; 424/4; 424/43; 424/44; 436/829; 128/653 R; 128/654; 252/315.3
[58] Field of Search ............ 436/829; 424/4, 43, 424/214, 9; 128/653, 654; 252/315.3

[56] References Cited

U.S. PATENT DOCUMENTS

| 4,192,859 | 3/1980 | Mackaness et al. | 424/4 |
| 4,344,929 | 8/1982 | Bonsen et al. | 424/44 |
| 4,544,545 | 10/1985 | Ryan et al. | 424/7.1 |
| 4,675,310 | 6/1987 | Chapman et al. | 514/76 |

FOREIGN PATENT DOCUMENTS 1009474  4/1983  U.S.S.R. .................. 424/4

OTHER PUBLICATIONS

MacNaughton et al., Biochim. Biophys. Acta 597 (1980), 193–198.
Gutknecht et al., Chemical Abstracts 87:34772q (1977).

Primary Examiner—Robert J. Warden
Assistant Examiner—Carol A. Spiegel
Attorney, Agent, or Firm—Paul J. Cook

[57] ABSTRACT

Phospholipid liposomes are provided having a lipid bilayer surrounding a confined composition which includes a gas or a gas precursor. The liposomes can be administered to a patient and can be detected in vivo by ultrasound techniques which permit organ imaging.

3 Claims, No Drawings

LIPISOMES CONTAINING GAS FOR ULTRASOUND DETECTION

BACKGROUND OF THE INVENTION

The present invention relates to the preparation of liposomes capable of providing reliable, clinically useful ultrasonographic contrast, by the inclusion of a gas or gas generating compound.

Liposomes are synthetic lipic vesicles whose lipid bilayers serve as a model of biomembranes. Liposomes can be prepared by a variety of techniques to yield vesicles of varying size and lamellar structure. They usually have a maximum diameter of the order of 100,000 Å, and most often have a diamter between 110 to 10,000 Å, bounded by a wall formed by at least one bimolecular layer (having a thickness of the order of 100 Å) of a compound of the general formula XY, where X is a hydrophilic polar group and Y is a hydrophobic non-polar group, the globules containing an aqueous liquid, for example, and aqueous solution of at least one biologically active substance, and existing generally in the form of a colloidal dispersion in an aqueous medium such as an aqueous saline solution, in particular a 0.9% by weight sodium chloride solution.

The preparation of liposomes provides a method of encapsulation which is most practical and effective for aqueous materials as well as hydrophobic and amphipathic material and which is particularly useful for administration of biologically active substances, particularly medicaments, into living organisms, while avoiding the destruction or inactivation of the substance in the organism, for example, by the action of gastric or intestinal juices, before the substances reach the site where they are required to act.

Central to this interest is an altered biodistribution of the agent to various organs, tissues or inflammatory sites.

Targeting of encapsulated material in liposomes has the advantage of increased specific activity of the agent to specific target site, lowered exposure of other areas to the agent thereby decreasing effective toxicity of the agent and altered time course of agent delivery. Loaded vesicles, therefore, hold promise of therapeutic and diagnostic use in cancer patients. Multilamellar as well as unilamellar lipid vesicles loaded with a radiopaque agent have been shown to enhance hepatic and splenic imaging of the rat by x-ray computed tomography.

By selection of the compound of formula XY used to form the wall of the liposomes, it is possible to produce liposomes having walls which resist the degradation by various physiological processes.

Typical processes for the preparation of liposomes include placing a lipid in contact with an aqueous liquid that is desired to be encapsulate and then warming the heterogeneous mixture thus obtained at a temperature slightly above ambient temperature and then submitting the mixture to vigorous agitation following ultrasonic vibration.

Another process consists of dissolving a compound of formula XY (where X and Y are defined above), for example, a lipid, in a volatile solvent, forming a film of the compound on the walls of a receptacle by evaporating the solvent form the solution thus obtained, introducing in the same receptacle the liquid which is desired to encapsulate in the liposomes, and finally submitting the liquid in the receptacle to the action of ultrasonic vibrations.

It would be highly desirable to provide a means for rendering liposomes more suitable for scanning a particular organ by means of ultrasound techniques without endangering the patient.

SUMMARY OF THE INVENTION

The present invention is based upon the discovery that liposomes containing a gas or material capable of forming a gas are highly suitable for being detected in vivo by conventional ultrasound detection processes or other diagnostic imaging modalities such as computed tomography. The liposomes are formed by conventional means but with the addition of a gas or gas precursor in the aqueous composition forming the liposome core. An aqueous composition containing the gas or gas precursor is admixed with a carrier liquid composition which is insoluble or only slightly soluble in water. The resultant mixture may be subjected to vigorous agitation such as ultrasonic agitation or prepared by emulsifying aqueous droplets containing the gas or gas precursor to be encapsulated in organic solvent, forming a gel by evaporation of solvent and addition of an aqueous phase to form the liposomes that can be unilamellar or multilamellar, the interior of which are filled with the gas or gas precursor. The resultant liposome is suitable for being detected in vivo by conventional ultrasound processes.

DESCRIPTION OF SPECIFIC EMBODIMENTS

In accordance with this invention, liposomes are provided which are characterized by the inclusion in the liposome core a gas or gas-forming composition so that the liposome is rendered highly suitable for being detected in vivo by conventional ultrasonic processes. The liposomes can be unilamellar or multilamellar and can be formed from any lipid material conventionally utilized to form liposomes. Representative suitable lipid materials that can be utilized to form liposomes include distearoyl phosphatidylcholine and/or L-$\alpha$-dipalmitoyl phosphatidylcholine or similar lipid substances. The walls of the liposomes can also be formed from soybean phospholipid, egg yolk lecithin and L-$\alpha$-dimyristoyl phosphatidylcholine. The liposomes may be prepared by simple sonication from liquid suspension, hydration of crystallized lipids or any other conventional procedure well known in the art. Generally, the liposomes have a size range of between about 0.001 and about 10 microns.

The aqueous portion of the liposome contains the gas or gas precursor which is to be delivered to the desired organ by the liposome. Representative suitable gaseous agents or gaseous precursors such as carbon dioxide, helium, argon, bicarbonates, aminomalonate, carbonates, xenon or the like which are useful in ultrasonography applications. The liposomes containing ag. Sodium Bicarbonate having a pH greater than about 7.5 are formed initially having an aqueous core. After being administered in vivo to a patient, a portion of the liposome core is converted to a gas by virtue of being exposed to the lower pH in the patient's body. It is preferred to utilize Sodium Bicarbonate or aminomalonate as the gas forming composition. The gas containing liposomes are capable of being detected easily in vivo because of its lower density as compared to the bodily organs.

After formation of the liposomes, they can be utilized by being suspended in a physiologically acceptable liquid such as saline and administered parenterally, orally, intramuscularly, subcutaneously, intraperitoneally, rectally, intralymphatically and intrathecally.

The following examples illustrate the present invention and are not intended to limit the same.

EXAMPLE 1

A quantity of 126 mg of egg lecithin and 27 mg of cholesterol are mixed in 9 ml of diethyl ether. 3 ml of 0.2 molar aqueous sodium bicarbonate solution is added and the resulting two phase system is sonicated until a homogenous suspension is obtained. The diethyl ether is removed by rotary evaporation, and the residue suspended in 0.2 molar aqueous sodium bicarbonate. Injection of a portion of this preparation (20%) into a rat via the lateral tail vein results on subsequent ultrasonographic scans to markedly increased echogenicity of the spleen and liver yielding a contrast enhancement of clinical significance.

EXAMPLE 2

The procedure of Example 1 was repeated except that the liposomes were acidified with 2N HCl to pH 2 and then neutralized to pH 6.0 with aqueous NaOH in order to form $CO_2$ gas in the liposomes prior to injecting them into a rat. The ultrasonic scans also gave markedly increased echogenicity.

We claim:

1. Phospholipid liposomes, for use as an ultrasound contrast medium, comprising an outer phospholipid layer and, confined by said layer a gas precursor selected from the group consisting of aqueous sodium bicarbonate and aqueous aminomalonate in an amount effective to form a gas under physiological pH conditions.

2. The liposomes of claim 1 wherein said gas precursor is aqueous sodium bicarbonate.

3. The liposomes of claim 1 wherein said gas precursor is aminomalonate.

* * * * *